(12) United States Patent
Addison et al.

(10) Patent No.: US 10,292,663 B2
(45) Date of Patent: May 21, 2019

(54) SYSTEM AND METHOD OF MONITORING AUTOREGULATION

(71) Applicant: COVIDIEN LP, Mansfield, MA (US)

(72) Inventors: Paul S. Addison, Edinburgh (GB); James N. Watson, Dunfermline (GB)

(73) Assignee: Covidien LP, Mansfield, MA (US)

( * ) Notice: Subject to any disclaimer, the term of this patent is extended or adjusted under 35 U.S.C. 154(b) by 330 days.

(21) Appl. No.: 15/194,122

(22) Filed: Jun. 27, 2016

(65) Prior Publication Data

US 2017/0000423 A1 Jan. 5, 2017

Related U.S. Application Data

(60) Provisional application No. 62/186,458, filed on Jun. 30, 2015.

(51) Int. Cl.
*A61B 5/00* (2006.01)
*A61B 5/021* (2006.01)
(Continued)

(52) U.S. Cl.
CPC ............ *A61B 5/7282* (2013.01); *A61B 5/021* (2013.01); *A61B 5/0205* (2013.01); *A61B 5/14551* (2013.01); *A61B 5/14553* (2013.01); *A61B 5/726* (2013.01); *A61B 5/742* (2013.01); *A61B 5/022* (2013.01); *A61B 5/0285* (2013.01);
(Continued)

(58) Field of Classification Search
CPC . A61B 5/7282; A61B 5/0205; A61B 5/14551; A61B 5/022; A61B 5/742; A61B 5/746; A61B 5/021; A61B 5/14533; A61B 5/02416; A61B 5/7221; A61B 5/7235; A61B 5/02108; A61B 5/55; A61B 5/0285; A61B 5/7278
See application file for complete search history.

(56) References Cited

U.S. PATENT DOCUMENTS

4,776,339 A    10/1988    Schreiber
5,218,962 A *   6/1993    Mannheimer ...... A61B 5/14542
                                                                                  356/41
(Continued)

FOREIGN PATENT DOCUMENTS

EP            615723 A1    9/1994
WO     WO9843071 A1    10/1998
(Continued)

OTHER PUBLICATIONS

Daubechies et al., "Synchrosqueezed wavelet transforms: an empirical mode decomposition-like tool". Applied and Computational Harmonic Analysis, vol. 30, Issue 2, Mar. 2011, pp. 243-261.*

(Continued)

*Primary Examiner* — Eric F Winakur
*Assistant Examiner* — Chu Chuan Liu
(74) *Attorney, Agent, or Firm* — Shumaker & Sieffert, P.A.

(57) ABSTRACT

A method for monitoring autoregulation includes receiving a blood pressure signal and an oxygen saturation signal, determining a phase difference between the blood pressure signal and the oxygen saturation signal, and determining a patient's autoregulation status based at least in part on a phase difference between the blood pressure signal and the oxygen saturation signal.

20 Claims, 6 Drawing Sheets

(51) Int. Cl.
*A61B 5/1455* (2006.01)
*A61B 5/0205* (2006.01)
*A61B 5/0225* (2006.01)
*A61B 5/0285* (2006.01)
*A61B 5/022* (2006.01)
*A61B 5/024* (2006.01)
*G16H 50/30* (2018.01)
*G16H 50/50* (2018.01)

(52) U.S. Cl.
CPC ....... *A61B 5/02108* (2013.01); *A61B 5/02255* (2013.01); *A61B 5/02416* (2013.01); *A61B 5/7221* (2013.01); *A61B 5/7235* (2013.01); *A61B 5/7278* (2013.01); *G16H 50/30* (2018.01); *G16H 50/50* (2018.01)

(56) References Cited

U.S. PATENT DOCUMENTS

| | | |
|---|---|---|
| 5,351,685 A | 10/1994 | Potratz |
| 5,482,034 A | 1/1996 | Lewis et al. |
| 5,533,507 A | 7/1996 | Potratz |
| 5,577,500 A | 11/1996 | Potratz |
| 5,584,296 A | 12/1996 | Cui et al. |
| 5,626,140 A | 5/1997 | Feldman et al. |
| 5,803,910 A | 9/1998 | Potratz |
| 5,934,277 A | 8/1999 | Mortz |
| 6,385,471 B1 | 5/2002 | Mortz |
| 6,438,399 B1 | 8/2002 | Kurth |
| 6,453,183 B1 | 9/2002 | Walker |
| 6,505,060 B1 | 1/2003 | Norris |
| 6,510,329 B2 | 1/2003 | Heckel |
| 6,599,251 B2 | 7/2003 | Chen et al. |
| 6,668,182 B2 | 12/2003 | Hubelbank |
| 6,714,803 B1 | 3/2004 | Mortz |
| 6,754,516 B2 | 6/2004 | Mannheimer |
| 6,896,661 B2 | 5/2005 | Dekker |
| 6,987,994 B1 | 1/2006 | Mortz |
| 7,001,337 B2 | 2/2006 | Dekker |
| 7,221,969 B2 | 5/2007 | Stoddart et al. |
| 7,268,873 B2 | 9/2007 | Sevick-Muraca et al. |
| 7,744,541 B2 | 6/2010 | Baruch et al. |
| 8,556,811 B2 | 10/2013 | Brady |
| 2004/0097797 A1 | 5/2004 | Porges et al. |
| 2005/0004479 A1 | 1/2005 | Townsend et al. |
| 2005/0033129 A1 | 2/2005 | Edgar, Jr. et al. |
| 2005/0192488 A1 | 9/2005 | Bryenton et al. |
| 2005/0192493 A1 | 9/2005 | Wuori |
| 2007/0004977 A1 | 1/2007 | Norris |
| 2007/0049812 A1 | 3/2007 | Aoyagi et al. |
| 2008/0081974 A1 | 4/2008 | Pav |
| 2008/0146901 A1 | 6/2008 | Katura et al. |
| 2008/0200785 A1 | 8/2008 | Fortin |
| 2008/0228053 A1 | 9/2008 | Wang et al. |
| 2009/0326386 A1 | 12/2009 | Sethi et al. |
| 2010/0010322 A1 | 1/2010 | Brady |
| 2010/0030054 A1 | 2/2010 | Baruch et al. |
| 2010/0049082 A1 | 2/2010 | Hu et al. |
| 2011/0046459 A1 | 2/2011 | Zhang et al. |
| 2011/0105912 A1 | 5/2011 | Widman et al. |
| 2012/0149994 A1 | 6/2012 | Luczyk et al. |
| 2012/0203087 A1* | 8/2012 | McKenna .......... A61B 5/14551 600/322 |
| 2012/0253211 A1 | 10/2012 | Brady et al. |
| 2012/0271130 A1 | 10/2012 | Benni |
| 2013/0190632 A1 | 7/2013 | Baruch et al. |
| 2014/0073888 A1 | 3/2014 | Sethi et al. |
| 2014/0275818 A1 | 9/2014 | Kassem et al. |
| 2014/0278285 A1 | 9/2014 | Marmarelis et al. |
| 2016/0106372 A1 | 4/2016 | Addison et al. |
| 2016/0324425 A1 | 11/2016 | Addison et al. |
| 2016/0345913 A1 | 12/2016 | Montgomery et al. |
| 2016/0367197 A1 | 12/2016 | Addison et al. |
| 2017/0000395 A1 | 1/2017 | Addison et al. |
| 2017/0095161 A1 | 4/2017 | Addison et al. |
| 2017/0105631 A1 | 4/2017 | Addison et al. |
| 2017/0105672 A1 | 4/2017 | Addison et al. |

FOREIGN PATENT DOCUMENTS

| | | |
|---|---|---|
| WO | WO0059374 | 10/2000 |
| WO | WO03000125 A1 | 1/2003 |
| WO | WO03071928 A2 | 9/2003 |
| WO | WO2004075746 A2 | 9/2004 |
| WO | WO2008097411 A1 | 8/2008 |
| WO | WO2016182853 A1 | 11/2016 |

OTHER PUBLICATIONS

International Search Report and Written Opinion of International Application No. PCT/US2016/039870, dated Nov. 7, 2016, 10 pp.
U.S. Appl. No. 15/666,167, filed Aug. 1, 2017, naming inventors Addison et al.
International Preliminary Report on Patentability from International Application No. PCT/US2016/039870, dated Jan. 11, 2018, 8 pp.
Gao Yuanjuin et al.; "Response of cerebral tissue oxygenation and arterial blood pressure to postural change assessed by wavelet phase coherence analysis", 2014 7th International conference on Biomedical Engineering and Informatics, IEEE, Oct. 14, 2014, pp. 373-377.
A.B. Rowley et al.; "Synchronization between arterial blood pressure and cerebral oxyhaemoglobin concentration investigated by wavelet cross-correlation; low-freqwuency MAP and 02Hb wavelet cross-correlation", Physiological Measurement, Institute of Physics Publishing,; vol. 28, No. 2, Feb. 1, 2007, pp. 161-173.
Matthias Reinhard et al.; "Spatial mapping of dynamic cerebral autoregulation by multichannel near-infrared spectrosccopy in high-grade carotid artery disease", International Society for optical Engineering, SPIE, vol. 19, No. 9, Sep. 1, 2014, p. 97005.
M. Reinhard et al.; "Oscillatory cerebral hemodynamics—the macro- vs. microvascular level", Journal of Neurological Sciences, Elsevier Scientific Publishing Col, vol. 250, No. 1-2, Dec. 1, 2006, pp. 103-109.
Ran Cheng et al.; "Noninvasive optical evaluation of spontaneous low frequency oscillations in cerebral hemodynamics", Neuroimage, Academic Press, vol. 62, No. 3, May 24, 2012, pp. 1445-1454.
International Search Report and Written Opinion for PCT Application No. PCT/US2016/039870 dated Nov. 7, 2016; 12 pgs.
Addison, P. S., et al.; "Low-Oscillation Complex Wavelets," Journal of Sound and Vibration, 2002, vol. 254, Elsevier Science Ltd., pp. 1-30.
Addison, P. S.; "The Illustrated Wavelet Transform Handbook," 2002, IOP Publishing Ltd., Bristol, UK, Ch. 2.
Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).
Barreto, Armando B., et al.; "Adaptive LMS Delay Measurement in dual Blood Volume Pulse Signals for Non-Invasive Monitoring," *IEEE*, pp. 117-120 (1997).
Bassan, Haim, et al.; "Identification of pressure passive cerebral perfusion and its mediators after infant cardiac surgery," Pediatric Research Foundation, vol. 57, No. 1, 2005; pp. 35-41.
Belal, Suliman Yousef, et al.; "A fuzzy system for detecting distorted plethysmogram pulses in neonates and paediatric patients," *Physiol. Meas.*, vol. 22, pp. 397-412 (2001).
Brady, Ken M., et al.; "Continuous Measurement of Autoregulation by Spontaneous Fluctuations in Cerebral Perfusion Pressure Comparison of 3 Methods," NIH Public Access Author Manuscript, Stroke, 2008, 39(9), pp. 1-13.
Brady, Ken M., et al.; "Continuous time-domain analysis of cerebrovascular autoregulation using near-infrared spectroscopy," American Stroke Association, DOI:10.1161/strokeaha.107.485706, Aug. 2007, pp. 2818-2825.
Brady, Ken M., et al.; "Monitoring cerebral blood flow pressure autoregulation in pediatric patients during cardiac surgery," Stroke 2010;41:1957-1962 (http://stroke.ahajournals.org/content/41/9/1957.full).

(56) References Cited

OTHER PUBLICATIONS

Brady, Ken M., et al.; "Noninvasive Autoregulation Monitoring with and without Intracranial Pressure in a Naïve Piglet Brain," Neuroscience in Anesthesiology and Perioperative Medicine, 2010, vol. 111, No. 1, International Anesthesia Research Society, pp. 191-195.

Brady, Kenneth, et al.; "Real-Time Continuous Monitoring of Cerebral Blood Flow Autoregulation Using Near-Infrared Spectroscopy in Patients Undergoing Cardiopulmonary Bypass," Stroke, 2010, 41, American Heart Association, Inc., pp. 1951-1956.

Caicedo, Alexander, et al.; "Cerebral Tissue Oxygenation and Regional Oxygen Saturation Can be Used to study Cerebral Autoregulation in Prematurely Born Infants," Pediatric Research, vol. 69, No. 6, Jun. 1, 2011, pp. 548-553.

Caicedo, Alexander, et al.; "Detection of cerebral autoregulation by near-infrared spectroscopy in neonates: performance analysis of measurement methods," Journal of Biomedical Optics 17 (11) pp. 117003-1-117003-9 (Nov. 2012).

Chan, K.W., et al.; "17.3: Adaptive Reduction of Motion Artifact from Photoplethysmographic Recordings using a Variable Step-Size LMS Filter," IEEE, pp. 1343-1346 (2002)+A10.

Chen, Li, et al.; "The role of pulse oximetry plethysmographic waveform monitoring as a marker of restoration of spontaneous circulation: a pilot study," Chin Crit Care Med, 2015, vol. 27, No. 3, pp. 203-208.

Chen, Liangyou, et al.; "IS respiration-induced variation in the photoplethysmogram associated with major hypovolemia in patients with actue tramatic injuries," Shock, vol. 34, No. 5, pp. 455-460 (2010).

Cheng, Ran, et al.; "Noninvasive optical evaluation of spontaneous low frequency oscillations in cerebral hemodynamics", Neuroimage, Academic Press, vol. 62, No. 3, May 24, 2012, pp. 1445-1454.

Coetzee, Frans M.; "Noise-Resistant Pulse Oximetry Using a Synthetic Reference Signal," IEEE Transactions on Biomedical Engineering, vol. 47, No. 8, Aug. 2000, pp. 1018-1026.

Cyrill, D., et al.; "Adaptive Comb Filter for Quasi-Periodic Physiologic Signals," Proceedings of the 25th Annual International Conference of the IEEE EMBS, Cancun, Mexico, Sep. 17-21, 2003; pp. 2439-2442.

Cysewska-Sobusaik, Anna; "Metrological Problems With noninvasive Transillumination of Living Tissues," Proceedings of SPIE, vol. 4115, pp. 15-24 (2001).

Czosnyka, Marek, et al.; "Monitoring of cerebrovascular autoregulation: Facts, Myths, and Missing Links," Neurocrit Care (2009) 10:373-386.

Daubechies, Ingrid, et al.; "A Nonlinear Squeezing of the Continuous Wavelet Transform Based on Auditory Nerve Models," Princeton University, 1996, Acoustic Processing Department, NY, pp. iii, 1-17.

Daubechies, Ingrid, et al.; "Synchrosqueezed Wavelet Transforms: an Empirical Mode Decomposition-like Tool," Princeton University, 2010, Applied and Computational Harmonic Analysis, pp. 1-32.

Dias, Celeste, et al.; "Optimal Cerebral Perfusion Pressure Management at Bedside: A Single-Center Pilot Study," Neurocritical care, vol. 23, No. 1, Jan. 8, 2015; pp. 92-102; ISSN: 1541-6933.

East, Christine E., et al.; "Fetal Oxygen Saturation and Uterine Contractions During Labor," American Journal of Perinatology, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," Proceedings of the 20th Annual International conference of the IEEE Engie in Medicine and Biology Society, vol. 20, No. 6, p. 3072-3075, 1998.

Eichhorn, Lars, et al.; "Evaluation of newar-infrared spectroscopy under apnea-dependent hypoxia in humans," Journal of Clinical Monitoring and Computing, vol. 29, No. 6, Feb. 4, 2015, pp. 749-757.

Ge, Z.; "Significance tests for the wavelet cross spectrum and wavelet linear coherence," Annales Geophysicae, 2008, 26, Copernicus Publications on behalf of European Geosciences Union, pp. 3819-3829.

Gesquiere, Michael J., et al., "Impact of withdrawal of 450 ML of blook on respiration-induced oscillations of the ear plethysmographic waveform," Journal of Clinical Monitoring and Computing (2007) 21:277-282.

Goldman, Julian M.; "Masimo Signal Extraction Pulse Oximetry," Journal of Clinical Monitoring and Computing, vol. 16, pp. 475-483 (2000).

Gommer, Erik D., et al.; "Dynamic cerebral autoregulation: different signal processing methods without influence on results and reproducibility"; Medical & Biological Engineering & Computer; vol. 48, No. 12, Nov. 4, 2010; pp. 1243-1250.

Hamilton, Patrick S., et al.; "Effect of Adaptive Motion-Artifact Reduction on QRS Detection," Biomedical Instrumentation & Technology, pp. 197-202 (May-Jun. 2000).

Huang, J., et al.; "Low Power Motion Tolerant Pulse Oximetry," Anesthesia & Analgesia 2002 94: S103.

Johansson, A.; "Neural network for photoplethysmographic respiratory rate monitoring," Medical & Biological Engineering & Computing, vol. 41, pp. 242-248 (2003).

Kaestle, S.; "Determining Artefact Sensitivity of New Pulse Oximeters in Laboratory Using Signals Obtained from Patient," Biomedizinische Technik, vol. 45 (2000).

Kim, J.M., et al.; "Signal Processing Using Fourier & Wavelet Transform for pulse oximetry," pp. II-310-II-311 (2001).

Kirkham, S.K., et al.; "A new mathematical model of dynamic cerebral autoregulation based on a flow dependent feedback mechanism; Dynamic cerebral autoregulation modelling," Physiological Measurement, Institute of Physics Publishing, vol. 22, No. 3, Aug. 1, 2001; (13 pgs.).

Leahy, Martin J., et al.; "Sensor Validation in Biomedical Applications," IFAC Modelling and Control in Biomedical Systems, Warwick, UK; pp. 221-226 (1997).

Lee, C.M., et al.; "Reduction of motion artifacts from photoplethysmographic recordings using wavelet denoising approach," IEEE EMBS Asian-Pacific Conference on Biomedical Engineering, Oct. 20-22, 2003; pp. 194-195.

Lee, Jennifer K., et al.; A pilot study of cerebrovascular reactivity autoregulation after pediatric cardiac arrest, Resuscitation 85, 2014, Elsevier Ireland Ltd., pp. 1387-1393.

Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).

Massart, Desire L., et al.; "Least Median of Squares: A Robust Method for Outlier and Model Error Detection in Regression and Calibration," Analytica Chimica Acta, 1986, Elsevier Science Publishers B.V., The Netherlands, pp. 171-179.

McGrath, S.P., et al.; "Pulse oximeter plethysmographic waveform changes in awake, spontaneously breathing, hypovolemic volunteers," Anesth. Analg. vol. 112 No. 2, pp. 368-74 (2010).

Montgomery, Dean, et al.; "Data cluestering methods for the determination of cerebral autoregulation functionality," Journal of Clinical Monitoring and Computing, vol. 30, No. 5, Sep. 16, 2015, pp. 661-668.

Morren, G., et al.; "Detection of autoregulation in the brain of premature infants using a novel subspace-based technique," 23rd Annual International Conference of IEEE Engineering in Medicine and Biology Society, Oct. 2001; pp. 1-4.

Morren, Geert, et al.; "Quantitation of the concordance between cerebral intravascular oxygenation and mean arterial blood pressure for the detection of impaired autoregulation," 29th Annual Meeting of the International Society on Oxygen Transport to Tissue, UofP, Aug. 2001; pp. 1-5.

Neumann, R., et al.; "Fourier Artifact suppression Technology Provides Reliable $SpO_2$," Anesthesia & Analgesia 2002, 94: S105.

Obrig, Hellmuth, et al.; "Spontaneous low frequency oscillations of cerebral heodynamics and metabolism in human adults," NeuroImage 12, 623-639 (2000).

(56) References Cited

OTHER PUBLICATIONS

Odagiri, Y.; "Pulse Wave Measuring Device," *Micromechatronics*, vol. 42, No. 3, pp. 6-11 (published Sep. 1998) (Article in Japanese—contains English summary of article).

Ono, Masahiro, et al.; "Validation of a stand-alone near-infrared spectroscopy system for monitoring cerebral autoregulaiton during cardiac surgery," International Anethesia Research Society, Jan. 2013, vol. 116, No. 1, pp. 198-204.

Panerai, B.; "Cerebral Autoregulation: from models to clinical Applications," Cardiovascular Engineering: an International Journal, vol. 8, No. 1, Nov. 28, 2007, (28 pgs.).

Payne, Stephen J., et al.; "Tissue Oxygenation Index as a Measure of Cerebral Autoregulation," Biomedial Engineering, Feb. 2004, Innsbruck, Austria, pp. 546-550.

Reinhard, Matthias, et al.; "Spatial mapping of dynamic cerebral autoregulation by multichannel near-infrared spectrosccopy in high-grade carotid artery disease", International Society for optical Engineering, SPIE, vol. 19, No. 9, Sep. 1, 2014, p. 97005.

Reinhard, Matthias, et al.; "Oscillatory cerebral hemodynamics— The macro- vs. microvascular level," Journal of the Neurological Sciences 250 (2006) 103-109.

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Rowley, A.B., et al.; "Synchronization between arterial blood pressure and cerebral oxyhaemoglobin concentration investigated by wavelet cross-correlation," Physiol. Meas., vol. 28, No. 2, Feb. 2007, pp. 161-173.

Shamir, M., et al.; "Pulse oximetry plethysmographic waveform during changes in blood volume," British Journal of Anaesthesia 82(2): 178-81 (1999).

Sorensen, Henrik, et al.; "A note on arterial to venous oxygen saturation as reference for NIRS-determined frontal lobe oxygen saturation in healthy humans," Frontiers in Physiology, vol. 4, Art. 403, Jan. 2014, pp. 1-3.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Such, Hans Olaf; "Optoelectronic Non-invasive Vascular Diagnostics Using multiple Wavelength and Imaging Approach," *Dissertation*, (1998).

Todd, Bryan, et al.; "The Identification of Peaks in Physiological Signals," *Computers and Biomedical Research*, vol. 32, pp. 322-335 (1999).

Tsuji, Miles, et al.; "Cerebral intravascular oxygenation correlates with mean arterial pressure in critically ill premature infants," American Academy of Pediatrics, 2000; 106; pp. 625-632.

Wagner, Bendicht P., et al.; "Dynamic cerebral autoregulatory response to blood pressure rise measured by near-infrared spectroscopy and intracranial pressure," Critical Care Medicine 2002, vol. 30, No. 9, pp. 2014-2021.

Whitaker, E., et al.; "Cerebrovascular Autoregulation After Pediatric Cardiac Arrest," NEURO-85, 2012, 2 pgs.

Williams, Monica, et al.; "Intraoperative blood pressure and Cerebral perfusion: strategies to clarify hemodynamic goals," Paediatric Anaesthesia, vol. 24, No. 7, Jul. 12, 2014; pp. 657-667; XP055331904.

Wong, Flora Y., et al.; "Impaired Autoregulation in preterm infants identified by using spatially resolved spectroscopy," American Academy of Pediatrics DOI:10.1542 (2008) e604-611.

Wu Dongmei, et al.; "Na*/H* Exchange inhibition delays the onset of hypovolemic circulatory shock in pigs," Shock, vol. 29, No. 4, pp. 519-525 (2008).

Wu, et al.; "Using synchrosqueezing transform to discover breathing dynamics from ECG signals," arXiv:1105.1571, vol. 2, Dec. 2013, pp. 1-9.

Wu, Hau-tieng, et al.; "Evaluating physiological dynamics via Synchrosqueezing: Prediction of Ventilator Weaning," Journal of Latex Class Files, vol. 11, No. 4, Dec. 2012, pp. 1-9.

Zhang, Rong, et al.; "Transfer function analysis of dynamic cerebral autoregulation in humans," 1998 the American Physiological Society; pp. H233-H241.

Zweifel, Christian, et al.; "Continuous time-domain monitoring of cerebral autoregulation in neurocritical care," Medical Engineering & Physics, Elsevier Ltd., vol. 36, No. 5, 2014, pp. 638-645.

U.S. Appl. No. 15/648,665, filed Jul. 13, 2017, Dean Montgomery.

Chuan et al., "Is cerebrovascular autoregulation associated with outcomes after major noncardiac surgery? A prospective observational pilot study," Acta Anaesthesiol Scand., Aug. 5, 2018, 10 pp.

\* cited by examiner

SYSTEM AND METHOD OF MONITORING AUTOREGULATION

CROSS-REFERENCE TO RELATED APPLICATION

This application claims priority to and the benefit of Provisional Application No. 62/186,458, entitled "SYSTEM AND METHOD OF MONITORING AUTOREGULATION," filed Jun. 30, 2015, which is herein incorporated by reference in its entirety for all purposes.

BACKGROUND

The present disclosure relates generally to medical devices and, more particularly, to systems and methods of monitoring autoregulation.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, medical professionals often desire to monitor certain physiological parameters of their patients. In some cases, clinicians may wish to monitor a patient's autoregulation. Autoregulation is a physiological process that attempts to maintain an optimal cerebral blood flow to supply appropriate levels of oxygen and nutrients to the brain. During autoregulation, cerebral arterioles dilate or constrict to maintain optimal blood flow. For example, as cerebral pressure decreases, cerebral arterioles dilate in an attempt to maintain blood flow. As cerebral pressure increases, cerebral arterioles constrict to reduce the blood flow that could cause injury to the brain. If the patient's autoregulation process is not functioning properly, the patient may experience inappropriate cerebral blood flow, which may have negative effects on the patient's health. In particular, a drop in cerebral blood flow may cause ischemia, which may result in tissue damage or death of brain cells. An increase in cerebral blood flow may cause hyperemia, which may result in swelling of the brain or edema.

Some existing systems for monitoring autoregulation may determine a patient's autoregulation status based on various physiological signals. For example, existing systems may determine a patient's autoregulation status based on a correlation between a change in blood pressure and a change in oxygen saturation. However, such a correlation may be subject to various sources of error. Accordingly, the autoregulation status determined by such existing systems may be inaccurate or unreliable.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
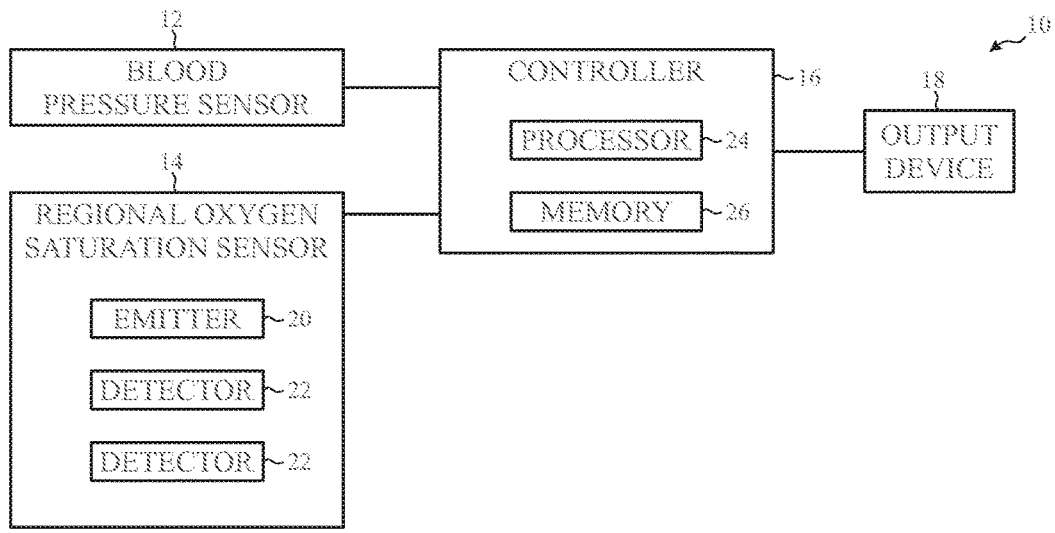
FIG. 1 is a block diagram of an embodiment of a system for monitoring a patient's autoregulation.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A physician may monitor a patient's autoregulation through the use of various monitoring devices and systems. In some cases, a patient's autoregulation may be monitored by correlating measurements of the patient's blood pressure (e.g., arterial blood pressure) with measurements of the patient's oxygen saturation (e.g., regional oxygen saturation). A cerebral oximetry index (COx) may be derived based at least in part on a linear correlation between the patient's blood pressure and oxygen saturation. However, the COx may be adversely affected by noise in the physiological signals, and/or may be adversely affected by other sources of error, such as a number of data points used in its computation, a gradient of a regression line, or the like. Thus, the COx may not accurately reflect the patient's autoregulation status.

In view of the foregoing, it may be desirable to determine (e.g., determine and/or assign) a confidence level (e.g., statistical confidence level, confidence measure, confidence metric, or quality metric) related to the COx. Accordingly, provided herein are systems and methods that enable determination of a confidence level of the COx. The confidence level may relate to, and provide some indication of, the accuracy and/or reliability of the COx (and thus, of the patient's autoregulation status). In certain embodiments, a system may determine the confidence level based at least in part on a phase difference between the blood pressure signal and the oxygen saturation signal. In particular, the phase difference between the blood pressure signal and the oxygen saturation signal may enable the system to determine that certain portions of the COx are reliable and/or accurate. The phase difference between the blood pressure signal and the oxygen saturation signal may also enable the system to identify certain portions of the COx that are unreliable and/or inaccurate.

In some embodiments, the system may be configured to provide information indicative of the confidence level to a user. For example, the system may provide a confirmation (e.g., via a display) that the autoregulation status is reliable if the COx is determined to have a high confidence level. In some cases, the system may discard portions of the COx that are determined to be unreliable or may take other remedial actions to provide accurate autoregulation information to the user, as discussed in more detail below. Such systems and methods may in turn provide improved patient monitoring and patient care.

FIG. 1 illustrates an embodiment of a system 10 for monitoring autoregulation. As shown, the system 10 includes a blood pressure sensor 12, an oxygen saturation sensor 14 (e.g., a regional oxygen saturation sensor), a controller 16, and an output device 18. The blood pressure sensor 12 may be any sensor or device configured to obtain the patient's blood pressure (e.g., arterial blood pressure). For example, the blood pressure sensor 12 may include a blood pressure cuff for non-invasively monitoring blood pressure or an arterial line for invasively monitoring blood pressure. In certain embodiments, the blood pressure sensor 12 may include one or more pulse oximetry sensors. In some such cases, the patient's blood pressure may be derived by processing time delays between two or more characteristic points within a single plethysmography (PPG) signal obtained from a single pulse oximetry sensor. Various techniques for deriving blood pressure based on a comparison of time delays between certain components of a single PPG signal obtained from a single pulse oximetry sensor is described in U.S. Publication No. 2009/0326386, entitled "Systems and Methods for Non-Invasive Blood Pressure Monitoring," the entirety of which is incorporated herein by reference. In other cases, the patient's blood pressure may be continuously, non-invasively monitored via multiple pulse oximetry sensors placed at multiple locations on the patient's body. As described in U.S. Pat. No. 6,599,251, entitled "Continuous Non-invasive Blood Pressure Monitoring Method and Apparatus," the entirety of which is incorporated herein by reference, multiple PPG signals may be obtained from the multiple pulse oximetry sensors, and the PPG signals may be compared against one another to estimate the patient's blood pressure. Regardless of its form, the blood pressure sensor 12 may be configured to generate a blood pressure signal indicative of the patient's blood pressure (e.g., arterial blood pressure) over time. As discussed in more detail below, the blood pressure sensor 12 may provide the blood pressure signal to the controller 16 or to any other suitable processing device to enable evaluation of the patient's autoregulation status.

As shown, the oxygen saturation sensor 14 may be a regional oxygen saturation sensor configured to generate an oxygen saturation signal indicative of blood oxygen saturation within the venous, arterial, and capillary systems within a region of the patient. For example, the oxygen saturation sensor 14 may be configured to be placed on the patient's forehead and may be used to calculate the oxygen saturation of the patient's blood within the venous, arterial, and capillary systems of a region underlying the patient's forehead (e.g., in the cerebral cortex). In such cases, the oxygen saturation sensor 14 may include an emitter 20 and multiple detectors 22. The emitter 20 may include at least two light emitting diodes (LEDs), each configured to emit at different wavelengths of light, e.g., red or near infrared light. In one embodiment, the LEDs of the emitter 20 emit light in the range of about 600 nm to about 1000 nm. In a particular embodiment, one LED of the emitter 20 is configured to emit light at about 730 nm and the other LED of the emitter 20 is configured to emit light at about 810 nm. One of the detectors 22 is positioned relatively "close" (e.g., proximal) to the emitter 20 and one of the detectors 22 is positioned relatively "far" (e.g., distal) from the emitter 22. Light intensity of multiple wavelengths may be received at both the "close" and the "far" detectors 22. For example, if two wavelengths are used, the two wavelengths may be contrasted at each location and the resulting signals may be contrasted to arrive at a regional saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Surface data from the skin and skull may be subtracted out, to generate a regional oxygen saturation ($rSO_2$) signal for the target tissues over time. As discussed in more detail below, the oxygen saturation sensor 14 may provide the regional oxygen saturation signal to the controller 16 or to any other suitable processing device to enable evaluation of the patient's autoregulation status. While the depicted oxygen saturation sensor 14 is a regional saturation sensor, the sensor 14 may be a pulse oximeter configured to obtain the patient's oxygen saturation or may be any suitable sensor configured to provide a signal indicative of the patient's blood flow. For example, the sensor 14 may be configured to emit light at a single wavelength (e.g., an isosbestic wavelength) and to provide a signal indicative of blood flow.

In operation, the blood pressure sensor 12 and the oxygen saturation sensor 14 may each be placed on the same or different parts of the patient's body. Indeed, the blood pressure sensor 12 and the oxygen saturation sensor 14 may in some cases be part of the same sensor or supported by a single sensor housing. For example, the blood pressure sensor 12 and the oxygen saturation sensor 14 may be part of an integrated oximetry system configured to non-invasively measure blood pressure (e.g., based on time delays in a PPG signal) and regional oxygen saturation. One or both of the blood pressure sensor 12 or the oxygen saturation sensor 14 may be further configured to measure other parameters, such as hemoglobin, respiratory rate, respiratory effort, heart rate, saturation pattern detection, response to stimulus such as bispectral index (BIS) or electromyography (EMG) response to electrical stimulus, or the like. While an exemplary system 10 is shown, the exemplary components illustrated in FIG. 1 are not intended to be limiting. Indeed, additional or alternative components and/or implementations may be used.

As noted above, the blood pressure sensor 12 may be configured to provide the blood pressure signal to the controller 16, and the oxygen saturation sensor 14 may be configured to provide the oxygen saturation signal to the controller 16. In certain embodiments, the controller 16 is an electronic controller having electrical circuitry configured to process the various received signals. In particular, the controller 16 may be configured to process the blood pressure signal and the oxygen saturation signal to evaluate the patient's cerebral autoregulation status. Although the blood pressure sensor 12 and the oxygen saturation sensor 14 may be configured to provide their respective signals or data directly to the controller 16, in certain embodiments, the signals or data obtained by the blood pressure sensor 12 and/or the oxygen saturation sensor 14 may be provided to one or more intermediate processing devices (e.g., specialized monitor, such as a blood pressure monitor or an oxygen saturation monitor, or the like), which may in turn provide processed signals or data to the controller 16.

In some embodiments, the controller 16 may be configured to determine a cerebral oximetry index (COx) based on the blood pressure signal and the oxygen saturation signal. The COx is indicative of vascular reactivity, which is related to cerebral blood vessels' ability to control proper blood flow, via vasoconstriction (a narrowing of the blood vessel) and/or vasodilation (expansion of the blood vessel), for example. Thus, the COx is also indicative of whether the patient's autoregulation is impaired. The controller 16 may derive the COx by determining a linear correlation between blood pressure measurements and oxygen saturation measurements. The linear correlation may be based on a Pearson coefficient, for example. The Pearson coefficient may be defined as the covariance of the measured blood pressure (e.g., arterial blood pressure) and oxygen saturation divided by the product of their standard deviations. The result of the linear correlation may be a regression line between oxygen saturation measurements and blood pressure measurements, and the slope of the regression line may be indicative of the patient's autoregulation status. In one implementation, a regression line with a relatively flat or negative slope (e.g., regional oxygen saturation remains the same or decreases after blood pressure increases) may suggest that cerebral autoregulation is working properly, while a regression line with a positive slope (e.g., regional oxygen saturation increases after blood pressure increases) may suggest that the cerebral autoregulation is impaired.

Figure 2:
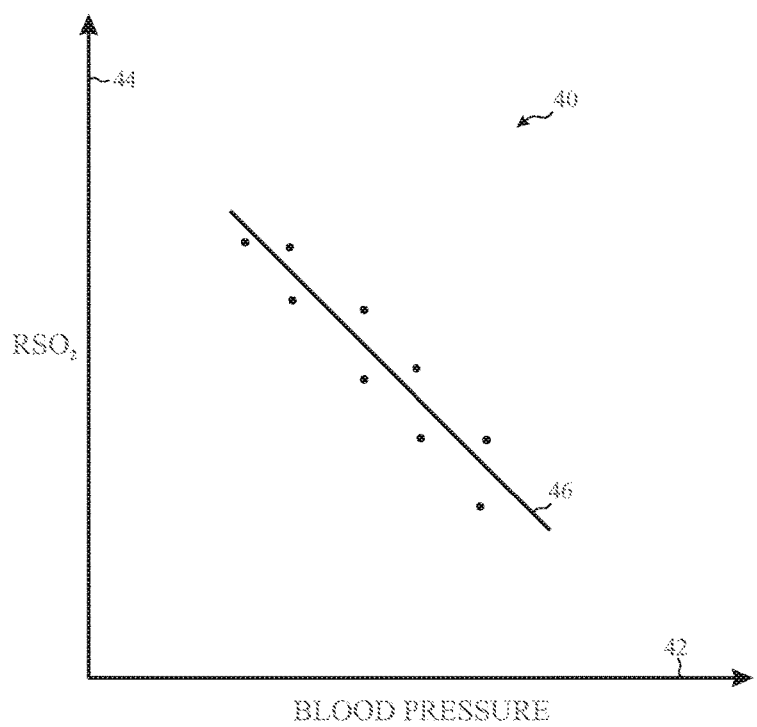
FIG. 2 is an example of a graph illustrating a linear correlation between oxygen saturation values and blood pressure values.

With the foregoing in mind, FIG. 2 is an example of a graph 40 illustrating a linear correlation between blood pressure measurements 42 (e.g., arterial blood pressure measurements) and oxygen saturation measurements 44. The result of the linear correlation may be a regression line 46 between the blood pressure measurements 42 and the oxygen saturation measurements 44, and the slope of the regression line 46 may be indicative of the patient's autoregulation status. In the illustrated example, the slope of the regression line 46 is negative and, thus, the COx value is between −1 and 0, which as discussed above, may indicate proper autoregulation. In such cases, the controller 16 may determine that the patient's cerebral autoregulation is functioning properly and may generate and/or output an appropriate signal indicative of the patient's autoregulation status to the output device 18, for example. However, when the regression line 46 has a positive slope and the COx value is between 0 and 1 or above some predetermined threshold between 0 and 1 (e.g., 0.1, 0.2, 0.3, 0.4, 0.5, 0.6, 0.7, 0.8, or 0.9), the controller 16 may determine that the patient's autoregulation is impaired and may generate and/or output the appropriate signal indicative of the patient's autoregulation status.

As discussed in more detail below, the controller 16 may also determine a phase difference between the blood pressure signal and the oxygen saturation signal. In such cases, the controller 16 may utilize the phase difference to determine whether the COx value is reliable or unreliable, in particular, a phase difference of approximately zero and/or a substantially constant phase difference may indicate correlation between the blood pressure signal and oxygen saturation signal, and thus, may indicate impaired autoregulation. However, a phase difference of approximately +/−π radians, and/or a rapidly varying and/or a randomly distributed phase difference, may indicate intact autoregulation. That is, the patient's blood flow (e.g., as indicated by the oxygen saturation signal) does not correlate with or is not driven by the patient's blood pressure, but rather, is controlled by the patient's autoregulation system to maintain appropriate blood flow. Thus, the phase difference may also be used to determine whether certain COx values, or portions of a COx signal generated based on such values, are reliable or unreliable. For example, if the COx signal over a time period indicates intact autoregulation (e.g., the COx is between −1 and 0), but the phase difference over the time period indicates impaired autoregulation (e.g., the phase difference is approximately 0 and/or constant), the controller 16 may determine that the corresponding portion of the COx signal is unreliable. In this way, the phase difference may enable the controller 16 to identify portions of the COx signal that are adversely affected by noise or processing errors, and which are therefore unreliable. In certain embodiments, the controller 16 may be configured to remove or discard the unreliable portions of the COx signal and/or take other appropriate remedial actions, as discussed in more detail below.

Returning to FIG. 1, in the illustrated embodiment, the controller 16 includes a processor 24 and a memory device 26. The controller 16 may also include one or more storage devices. The processor 24 may be used to execute software, such as software for carrying out any of the techniques disclosed herein, such as processing the blood pressure signals and/or oxygen saturation signals, determining a phase difference, analyzing the phase difference, determining the COx, determining a confidence level of the COx, carrying out appropriate remedial actions, and so forth. Moreover, the processor 24 may include multiple microprocessors, one or more "general-purpose" microprocessors, one or more special-purpose microprocessors, and/or one or more application specific integrated circuits (ASICS), or some combination thereof. For example, the processor 24 may include one or more reduced instruction set (RISC) processors.

The memory device 26 may include a volatile memory, such as random access memory (RAM), and/or a nonvolatile memory, such as ROM. The memory device 26 may include one or more tangible, non-transitory, machine-readable media collectively storing instructions executable by the processor 24 to perform the methods and control actions described herein. Such machine-readable media can be any available media that can be accessed by the processor 24 or by any general purpose or special purpose computer or other machine with a processor. The memory device 26 may store a variety of information and may be used for various purposes. For example, the memory device 26 may store processor-executable instructions (e.g., firmware or software) for the processor 24 to execute, such as instructions for carrying out any of the techniques discloses herein, such as processing the blood pressure signal and/or the oxygen saturation signal, determining a phase difference, analyzing the phase difference, determining the COx, determining a confidence level of the COx, and/or taking appropriate remedial actions (e.g., output a visual or audible indication that the autoregulation status is unavailable or unreliable, block output of the COx, or the like). The storage device(s) (e.g., nonvolatile storage) may include read-only memory (ROM), flash memory, a hard drive, or any other suitable optical, magnetic, or solid-state storage medium, or a combination thereof. The storage device(s) may store data (e.g., the blood pressure signal, the oxygen saturation signal, the COx, the phase map, the phase difference, etc.), instructions (e.g., software or firmware for processing the blood pressure signal and/or the oxygen saturation signal, determining a phase difference, analyzing the phase difference, determining the COx, determining a confidence level of the COx, and/or taking appropriate remedial actions), predetermined thresholds, and any other suitable data.

As shown, the system 10 includes the output device 18. In some embodiments, the controller 16 may be configured to provide signals indicative of the patient's autoregulation status to the output device 18. As discussed in more detail below, the controller 16 may be configured to generate an alarm signal indicative of the patient's autoregulation status and to provide the alarm signal to the output device 18. The output device 18 may include any device configured to receive signals (e.g., the signal indicative of the patient's autoregulation status, the alarm signal, the signal indicative of a confidence level, or the like) from the controller 16 and visually and/or audibly output information indicative of the patient's autoregulation status (e.g., the COx, the COx signal, the phase difference, the confidence level of the COx, an alarm, or the like). For instance, the output device 18 may include a display configured to provide a visual representation of the patient's autoregulation status, the COx, and/or the confidence level as determined by the controller 16. Additionally or alternatively, the output device 18 may include an audio device configured to provide sounds in accordance with the patient's autoregulation status, the COx, and/or the confidence level. The output device 18 may be any suitable device for conveying such information, including a computer workstation, a server, a desktop, a notebook, a laptop, a handheld computer, a mobile device, or the like. In some embodiments, the controller 16 and the output device 18 may be part of the same device or supported within one housing (e.g., a computer or monitor).

Figure 3:
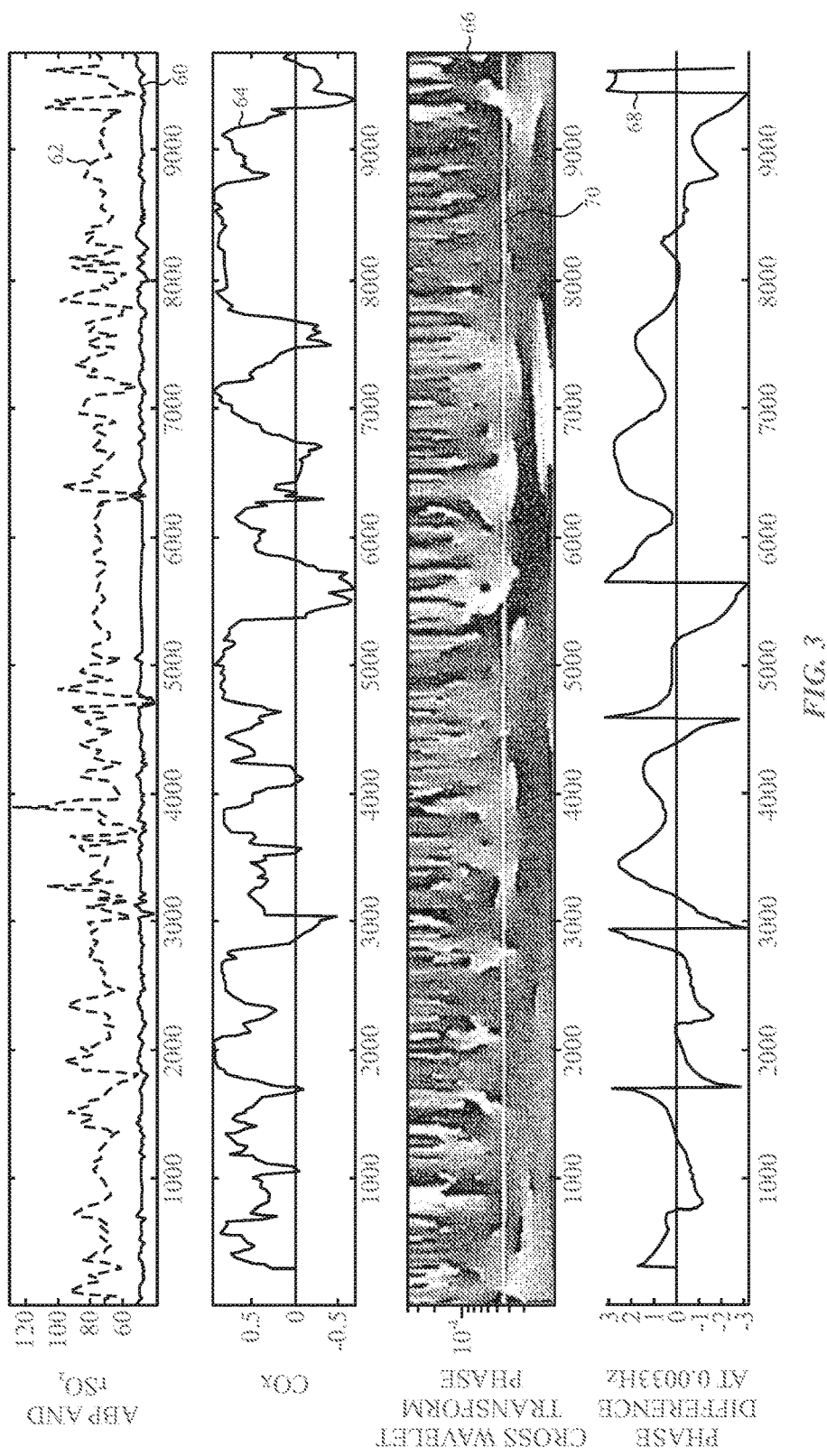
FIG. 3 is an example of a series of graphs illustrating blood pressure, oxygen saturation, a cerebral oximetry index (COx), a phase map, and a phase difference over time.

As noted above, a phase difference between the blood pressure signal and the oxygen saturation signal may be indicative of the patient's autoregulation status. Thus, in accordance with certain embodiments of the present disclosure, the phase difference may be utilized to determine a confidence level related to the COx. The phase difference may be determined in any of a variety of manners. For example, in some embodiments, the phase difference may be determined based on a cross-wavelet transform of the blood pressure signal and the oxygen saturation signal. With the foregoing in mind, FIG. 3 is an example of a series of graphs illustrating a blood pressure signal 60, an oxygen saturation signal 62, a cerebral oximetry index (COx) 64, a phase map 66 (i.e., a phase map generated from a cross-wavelet transform of the blood pressure signal 60 and the oxygen saturation signal 62), and a phase difference 68 (i.e., a phase difference at a characteristic frequency over time). The phase map 66 is indicative of the phase difference between the blood pressure signal and the oxygen saturation signal across a range of scales (or frequencies) and temporal locations. In the illustrated embodiment, a characteristic frequency level of 0.0033 Hz is shown by a line 70 drawn across the phase map 66, and the phase difference 68 is derived from the cross-wavelet transform at the characteristic frequency level (e.g., 0.0033 Hz or any suitable characteristic frequency). The characteristic frequency level may be predetermined (e.g., stored in the memory device 26 and accessed by the processor 24) and/or may be selected by a user (e.g., via inputs communicatively coupled to the controller 16).

The wavelet function used to calculate the phase difference may be selected to optimize the temporal or frequency support required for the desired resolution and/or smoothing. In some embodiments, a low oscillation wavelet may be utilized. For example, FIG. 3 illustrates a low oscillation Morlet wavelet with a central frequency ($\omega_0$) of 3 radians per second, which may provide sufficient resolution. In certain embodiments, a low oscillation wavelet with a central frequency of approximately 1, 2, 3, or 4 radians per second may be utilized to calculate the phase difference. In some embodiments, a low oscillation wavelet with a central frequency of less than approximately 5 radians per second may be utilized, as high central frequencies may cause the phase information to become smoothed over time and provide insufficient resolution for evaluation of the COx and/or the patient's autoregulation. Although the examples provided herein relate to wavelet transforms, it should be understood that any techniques, including any suitable complex transform (e.g., a Fourier transform), may be utilized to determine a phase difference between the blood pressure signal and the oxygen saturation signal.

Figure 4:
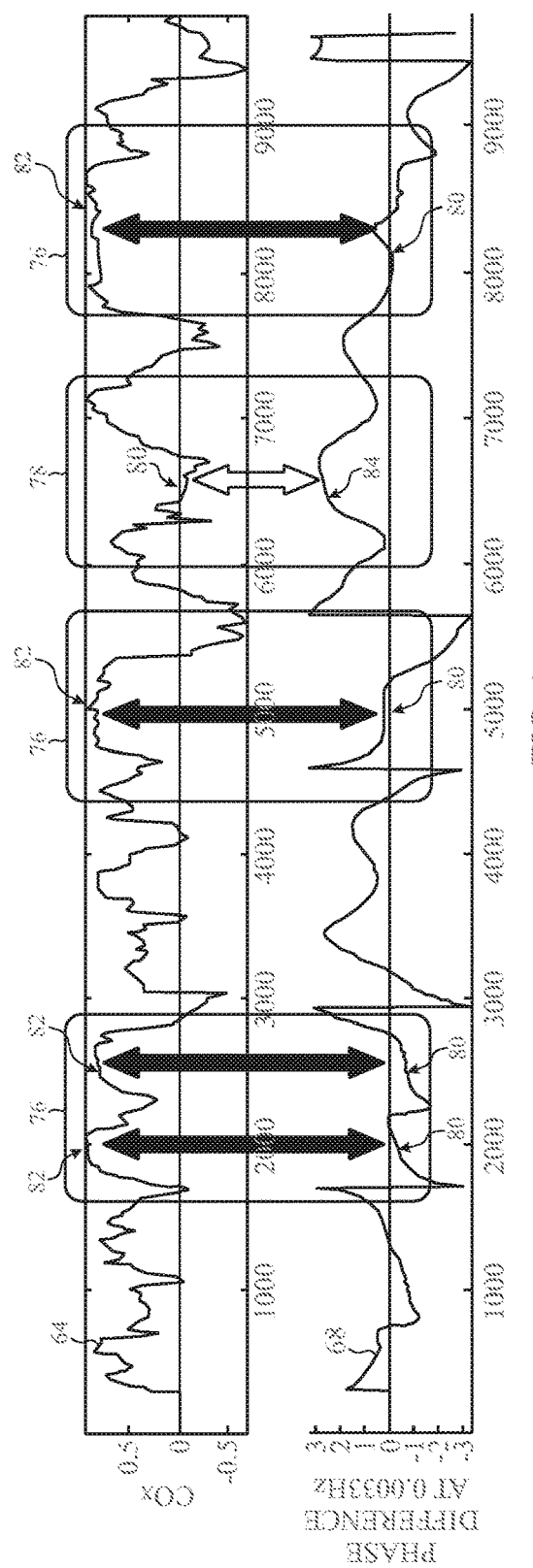
FIG. 4 is an example of a series of graphs illustrating a correlation between COx and a phase difference over time.

FIG. 4 illustrates an example of correlations between the COx 64 and the phase difference 68. In sections 76, regions 80 of approximately zero phase difference generally correlate with regions 82 of high COx values. When the phase difference is approximately zero and/or stable over a period of time coinciding with a high or positive COx value (e.g., between 0 and 1), as in sections 76, the controller 16 may determine that the COx value has a high confidence level (and thus, that the patient's autoregulation is impaired). Additionally, in section 78, a region 84 of a phase difference of approximately $\pi$ radians generally correlates with a region 86 of near-zero COx values. When the phase difference is approximately $+/-\pi$ radians over a period of time coinciding with a low or negative COx value (e.g., between −1 and 0), the controller 16 may determine that the COx value has a high confidence level (and thus, that the patient's autoregulation is intact). On the other hand, if the phase difference does not corroborate the COx as set forth above, the controller 16 may determine that the COx value has a low confidence level or is unreliable. Accordingly, the phase difference 68 may be useful in providing a confidence level for the COx 64.

As discussed in more detail below, the controller 16 may be configured to remove or discard unreliable COx values (e.g., COx values having a low confidence level) and/or take other appropriate remedial action when the COx value is unreliable. For example, the controller 16 may not output the COx signal 64 or the signal indicative of the patient's autoregulation status while the phase difference does not corroborate the COx. In some cases, the controller 16 may cause the output device 18 to display a blank display screen or provide an appropriate visual or audible indication that the COx signal 64 is unavailable. In certain embodiments, the controller 16 may hold or maintain the COx value immediately preceding the segment determined to be unreliable, and thus may cause the output device 18 to show the most recent reliable COx signal 64 for a set period of time or until the phase difference indicates that the COx is reliable. In some embodiments, the controller 16 may be configured to average the unreliable COx value(s) with the most recent reliable COx value(s), and may cause the output device 18 to provide an appropriate visual or audible indication of this average COx value. In some embodiments, when the controller 16 determines that the phase difference corroborates the COx (e.g., a high confidence level in the COx), the controller 16 may cause the output device 18 to provide a visual or audible indication of the patient's autoregulation status and/or that the COx signal 64 is reliable.

Furthermore, in certain embodiments, the phase difference may be utilized to weight the COx values within a moving average. For example, high confidence (e.g., greater than approximately 50, 90, 95, or 99 percent) COx values may receive a relatively higher weight than low confidence (e.g., less than approximately 50, 90, 95, or 99 percent) COx values in an ensemble averaging technique. In some embodiments, the weight applied to the COx values may be on a sliding scale, such that intermediate confidence (e.g., greater than approximately 50, 90, or 95 percent) COx values receive a relatively lower weight than high confidence COx values and a relatively higher weight than relatively low confidence COx values. In some embodiments, the desired level of confidence may be predetermined (e.g., stored in the memory device 26) and/or selected (e.g., via inputs coupled to the controller 16) by a user. In some embodiments, a trigonometric function may be utilized to compensate for phase wrap and to bound the value used to indicate correlation, thus making it easier to identify regions of various phase differences. For example, a cosine of the phase difference will provide a value of 1 for phase differences of approximately 0 and will provide a value of −1 for phase differences of approximately +/−π radians. Such values may be further transformed to alter the limits of the function output (e.g., $0.5*(\cos(\varphi)+1)$) to limit the output to 0 to 1 to facilitate identification of regions of various phase differences.

Although certain examples provided herein utilize the phase difference to assess the quality of the COx, in some embodiments, the phase difference may be used to determine a confidence level for other measures of autoregulation, such as a mean velocity index (Mx) and/or a pressure reactivity index (PRx). Thus, a phase difference of approximately zero and/or a substantially constant phase difference may provide high confidence in the Mx and/or the PRx indicating impaired autoregulation, while a phase difference of approximately +/−π radians, and/or a rapidly varying and/or a randomly distributed phase difference, may provide high confidence in the Mx and/or the PRx indicating intact autoregulation. In a similar manner as discussed above with respect to COx, low confidence in the Mx and/or the PRx may be indicated if the phase difference does not corroborate the Mx and/or the PRx values. Furthermore, while the examples provided herein utilize the phase difference to assess the quality of the COx value and/or other autoregulation metrics, in some embodiments, the phase difference may be used to directly monitor the patient's autoregulation. For example, if the phase difference is approximately zero and/or generally stable over a period of time, the controller 16 may determine that the patient's autoregulation is impaired, and if the phase difference is approximately +/−π radians, and/or rapidly varying and/or randomly distributed, over a period of time, the controller 16 may determine that the patient's autoregulation is intact.

Figure 5:
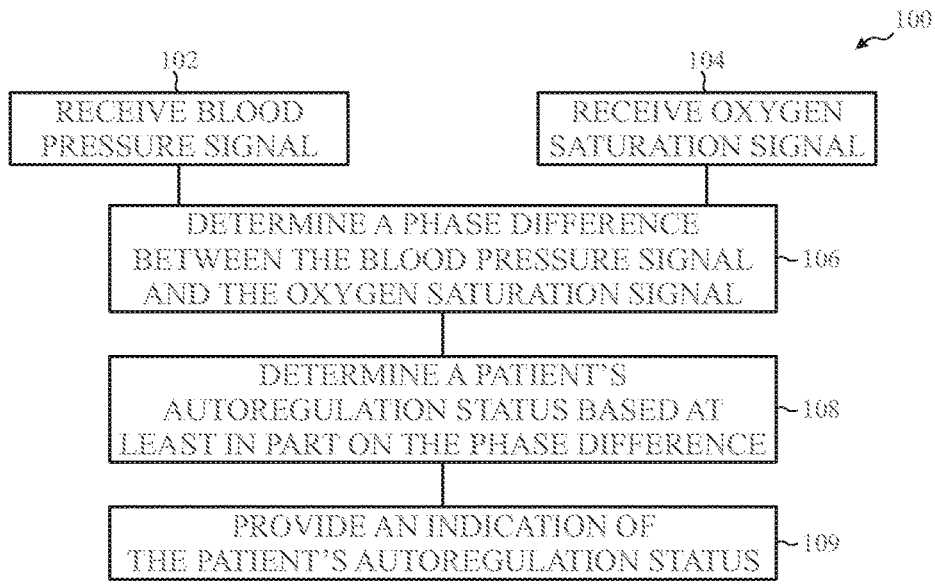
FIG. 5 is a process flow diagram of a method of monitoring autoregulation based at least in part on a phase difference between an oxygen saturation signal and a blood pressure signal, in accordance with an embodiment.
Figure 6:
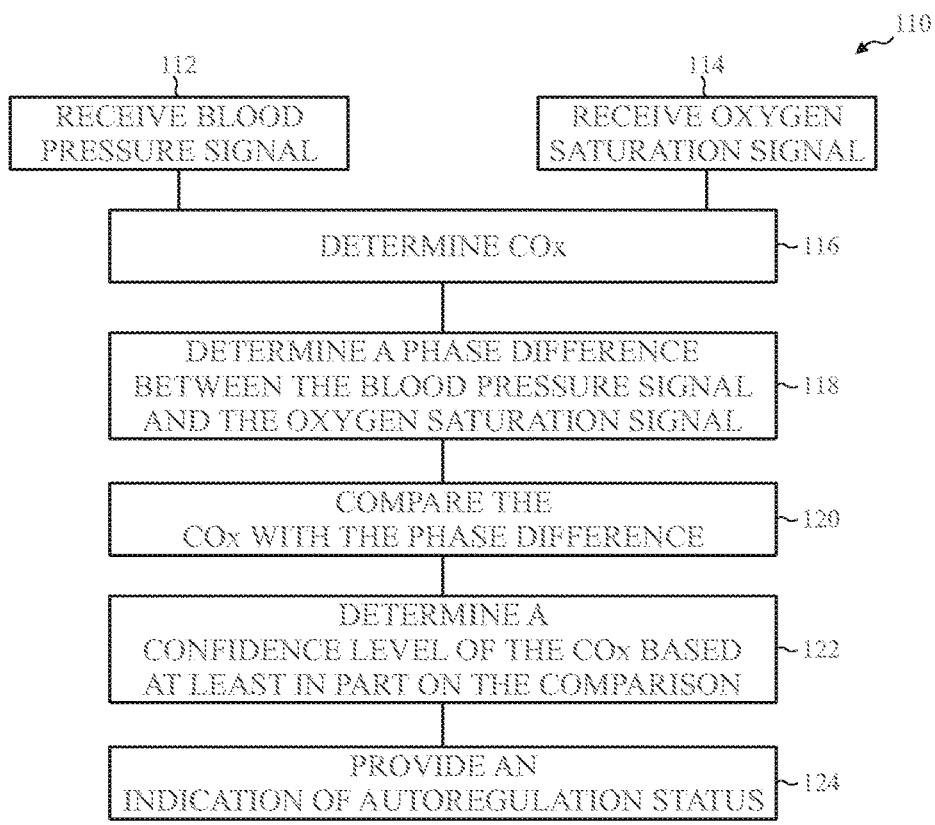
FIG. 6 is a process flow diagram of a method of determining a confidence level related to the COx based at least in part on a comparison of the COx to a phase difference between an oxygen saturation signal and a blood pressure signal, in accordance with an embodiment.
Figure 8:
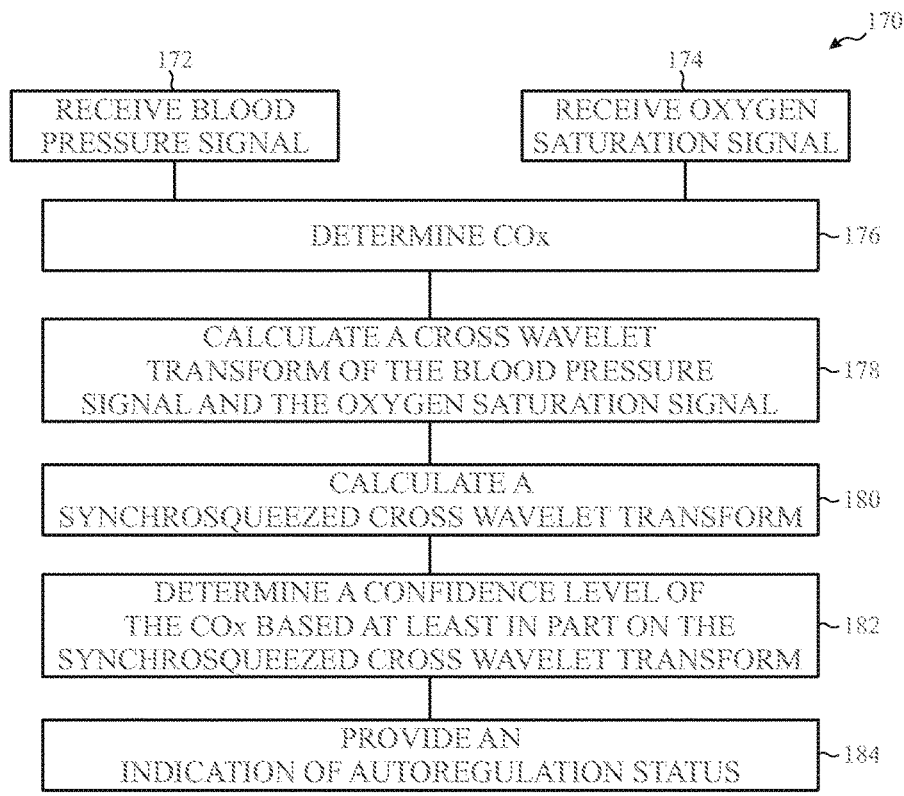
FIG. 8 is a process flow diagram of a method of monitoring autoregulation using a synchrosqueezed cross-wavelet transform, in accordance with an embodiment.

FIGS. 5, 6, and 8 are flow charts illustrating various methods for monitoring autoregulation, in accordance with the present disclosure. The methods include various steps represented by blocks. It should be noted any of the methods provided herein, may be performed as an automated procedure by a system, such as system 10. Although the flow charts illustrate the steps in a certain sequence, it should be understood that the steps may be performed in any suitable order and certain steps may be carried out simultaneously, where appropriate. Further, certain steps or portions of the methods may be performed by separate devices. For example, a first portion of the method may be performed by the controller 16, while a second portion of the method may be performed by the sensor 14. In addition, insofar as steps of the methods disclosed herein are applied to the received signals, it should be understood that the received signals may be raw signals or processed signals. That is, the methods may be applied to an output of the received signals.

FIG. 5 is a process flow diagram of a method 100 of monitoring autoregulation based at least in part on a phase difference between the oxygen saturation signal and the blood pressure signal, in accordance with an embodiment. Some or all of the steps of the method 100 may be implemented by the controller 16 (e.g., the processor 24 of the controller 16) of FIG. 1, for example, to determine whether the patient's autoregulation is impaired and/or to take an appropriate remedial action (e.g., output a visual or audible indication that the autoregulation status is unavailable or unreliable, block output of the COx, or the like). In step 102, the controller 16 may receive the blood pressure signal (e.g., arterial blood pressure signal). In some embodiments, the controller 16 may receive the blood pressure signal from the blood pressure sensor 12, as set forth above. In step 104, the controller 16 may receive the oxygen saturation signal. In some embodiments, the controller 16 may receive the oxygen saturation signal from the oxygen saturation sensor 14, as set forth above.

In step 106, the controller 16 may determine a phase difference between the blood pressure signal and the oxygen saturation signal. As set forth above, the controller 16 may determine the phase difference using any of a variety of suitable techniques. For example, in some embodiments, the controller 16 may calculate the phase difference using a cross-wavelet transform, as discussed above. In step 108, the controller 16 may determine the patient's autoregulation status based at least in part on the phase difference. As previously noted, the controller 16 may utilize the phase difference to directly monitor the patient's autoregulation status. In such cases, an approximately zero and/or constant phase difference may indicate impaired autoregulation, while a phase difference of +/−π radians, and/or a rapidly varying and/or randomly distributed phase difference, may indicate properly functioning autoregulation. In certain embodiments, the phase difference may be used in conjunction with one or more autoregulation measurements, such as COx, Mx, and/or PRx, to determine the patient's autoregulation status. For example, in some such embodiments, the phase difference may be used to determine a confidence level of the COx, Mx, and/or PRx as part of the autoregulation analysis, as set forth in more detail with respect to FIG. 6.

In step 109, the controller 16 may provide an indication of the patient's autoregulation status to the output device 18. For example, in some cases, the controller 16 may cause the output device 18 to provide a visual and/or audible indication of proper autoregulation if the phase difference is approximately +/−π radians, and/or a rapidly varying and/or randomly distributed. Furthermore, the controller 16 may cause the output device to 18 to provide a signal indicating impaired autoregulation if the phase difference is approximately zero and/or constant. Additional or alternative steps related to indications provided to the output device 18 are discussed below with respect to FIG. 6.

FIG. 6 is a process flow diagram of a method 110 of determining a confidence level related to the COx based at least in part on a comparison of the COx to a phase difference between an oxygen saturation signal and a blood pressure signal, in accordance with an embodiment. Some or all of the steps of the method 110 may be implemented by the controller 16 (e.g., the processor 24 of the controller 16) of FIG. 1, for example, to determine whether the patient's autoregulation is impaired. In step 112, the controller 16 may receive the blood pressure signal (e.g., arterial blood pressure signal). In some embodiments, the controller 16 may receive the blood pressure signal from the blood pressure sensor 12, as set forth above. In step 114, the controller 16 may receive the oxygen saturation signal. In some embodiments, the controller 16 may receive the oxygen saturation signal from the oxygen saturation sensor 14, as set forth above.

In step 116, the controller 16 may determine the COx based on the linear correlation between blood pressure measurements of the blood pressure signal and the oxygen saturation measurements of the oxygen saturation signal. In step 118, the controller 16 may determine a phase difference between the blood pressure signal and the oxygen saturation signal. The phase difference may be determined via any suitable technique, including those discussed above with respect to FIGS. 2-5, for example. In step 120, the controller 16 may compare the COx to the phase difference. As noted above, regions of high or positive COx values (e.g., between 0 and 1) are expected to correlate with regions of approximately zero and/or constant phase difference. Additionally, regions of near-zero and/or low COx values (e.g., between −1 and 0) are expected to correlate with regions of a phase difference of approximately +/−π radians and/or a rapidly varying and/or randomly distributed phase difference.

In step 122, the controller 16 may determine a confidence level related to the COx based at least in part on the comparison between the phase difference and the COx. For example, when the phase difference is approximately zero over a period of time coinciding with a high or positive COx value (e.g., between 0 and 1), the controller 16 may determine that the COx value has a high confidence level (e.g., greater than approximately 50, 90, 95, or 99 percent), and thus, that the patient's autoregulation is impaired. Similarly, when the phase difference is approximately +/−π radians over a period of time coinciding with a low or negative COx value (e.g., between −1 and 0), the controller 16 may determine that the COx value has a high confidence level (e.g., greater than approximately 50, 90, 95, or 99 percent), and thus, that the patient's autoregulation is intact. However, if the phase difference does not corroborate the COx as set forth above, the controller 16 may determine that the COx value has a low confidence level (e.g., less than approximately 50, 90, 95, or 99 percent) or is unreliable.

In step 124, the controller 16 may provide an indication of autoregulation status. For example, the controller 16 may cause the output device 18 to provide a visual or audible indication of the autoregulation status (e.g., functioning or impaired), the COx, the phase difference, and/or a confidence level. In some cases, when the controller 16 determines that the phase difference corroborates the COx, the controller 16 may cause the output device 18 to provide a visual or audible indication that the signal indicative of the patient's autoregulation status and/or the COx signal 64 has a high confidence level and/or is reliable. In certain embodiments, while the phase difference does not corroborate the COx, the controller 16 may not output the COx signal 64 and/or the signal indicative of the patient's autoregulation status. Additionally or alternatively, the controller 16 may cause the output device 18 to display a blank display screen or provide an appropriate visual or audible indication that the COx signal 64 is unavailable. Additionally or alternatively, the controller 16 may hold or maintain the COx value immediately preceding the segment determined to be unreliable, and thus may cause the output device 18 to show the most recent reliable COx signal 64 for a set period of time or until the phase difference indicates that the COx is reliable. Additionally or alternatively, the controller 16 may be configured to weight the COx value(s) based on the phase difference and/or average the unreliable COx value(s) with the most recent reliable COx value(s), and may cause the output device 18 to provide an appropriate visual or audible indication of this average COx value.

In some embodiments, additional or alternative processing techniques may be utilized to determine the patient's autoregulation status. For example, cross-wavelet transform components may be reassigned via a synchrosqueezing process to facilitate determination of the patient's autoregulation status and/or to facilitate determination of a confidence level related to the COx. With the foregoing in mind, the cross-wavelet transform of two signals (f and g) may be expressed in complex exponential form as:

$$\mathrm{CrWT}_{fg}(a,b) = |T_f(a,b)||T_g(a,b)|e^{i(\Phi_g(a,b)-\Phi_f(a,b))} \tag{1}$$

where a and b are scale and time variables, respectively, $T_f(a,b)$ and $T_g(a,b)$ are the wavelet coefficients of the time series f(t) and g(t), respectively, and $\Phi_g(a,b)-\Phi_f(a,b)$ is the phase angle. As shown by Equation 1, the phase angle ($\Phi_g(a,b)-\Phi_f(a,b)$) of the cross-wavelet transform reflects the phase difference between transforms of the individual signals (e.g., the phase difference by which f(t) leads g(t) at the given scale and time. Therefore, the cross-wavelet transform phase may provide a phase difference map between the two signals over a range of scales (or frequencies) and temporal locations. In some embodiments, components in the cross-wavelet transform domain may be reassigned through synchrosqueezing. Synchrosqueezing may identify an instantaneous frequency for each point in the transform domain as follows:

$$f_t = \frac{1}{2\pi} \frac{\partial \phi(a,b)}{\partial b} \tag{2}$$

where a and b are scale and time variables, respectively, and φ is the phase angle. The derivative of the phase angle with respect to time is the frequency of phase cycling corresponding to the transform component at that point in the transform domain and may be used to move transform components to a new location corresponding to $f_t$.

Figure 7:
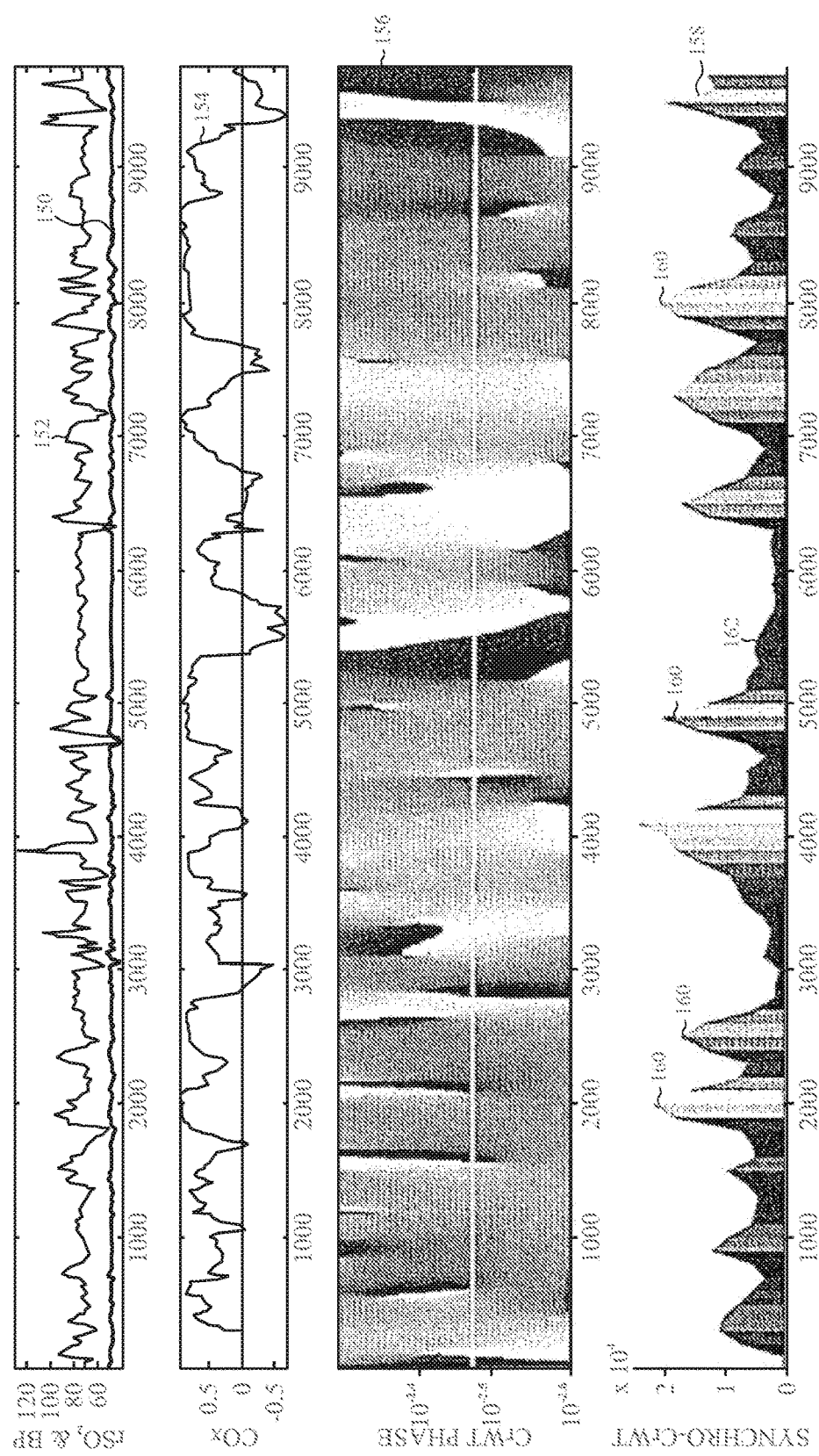
FIG. 7 is an example of a series of graphs illustrating blood pressure, oxygen saturation, a phase map, and a synchrosqueezed phase map.

With the foregoing in mind, FIG. 7 is an example of a series of graphs illustrating a blood pressure signal 150, an oxygen saturation signal 152, a COx signal 154, a phase map 156 (i.e., CrWT phase, a phase map generated from a cross-wavelet transform of the blood pressure signal 150 and the oxygen saturation signal 152), and a synchrosqueezed cross-wavelet transform 158 (i.e., Synchro-CrWT) at a zero-frequency level. As discussed above, an approximately zero and/or constant phase difference between the blood pressure signal 150 and the oxygen saturation signal 152 may indicate impaired autoregulation, while a phase difference of +/−π radians, and/or a rapidly varying and/or randomly distributed phase difference, may indicate properly functioning autoregulation. In the synchrosqueezed cross-wavelet transform 158, stable phase differences between the blood pressure signal 150 and the oxygen saturation signal 152 manifest as significant energy at the zero-frequency level, thereby facilitating identification of regions of stable, or relatively constant, phase differences. In some embodiments, energies at, or around zero phase, may be normalized by dividing by a total energy in the signal, or within a sub-band of the signal.

Features of the synchrosqueezed cross-wavelet transform 158 may be utilized to evaluate the patient's autoregulation status. For example, in some embodiments, the controller 16 may determine that a patient's autoregulation system is impaired if the synchrosqueezed cross-wavelet transform indicates significant energy at the zero-frequency level, such as in regions 160. In some cases, the controller 16 may determine that a patient's autoregulation system is intact if the synchrosqueezed cross-wavelet transform lacks regions of region 162, or otherwise indicates a phase difference of approximately +/−π radians, and/or a rapidly varying and/or randomly distributed phase difference.

Furthermore, in some embodiments, the synchrosqueezed cross-wavelet transform may be utilized to determine a confidence level of the COx. As noted above, regions of approximately zero and/or constant phase difference are expected to correlate with regions of high or positive COx values. Additionally, regions having a phase difference of approximately +/−π radians, and/or a rapidly varying and/or randomly distributed phase difference, are expected to correlate with regions of low or negative COx values. Accordingly, when the synchrosqueezed cross-wavelet transform includes significant energy at the zero-frequency level over a period of time coinciding with a high or positive COx value (e.g., between 0 and 1), such as in regions 160, the controller 16 may determine that the COx value has a high confidence level (e.g., greater than 50, 90, 95, or 99 percent), and thus, that the patient's autoregulation is impaired. Similarly, when the synchrosqueezed cross-wavelet transform indicates low enemy at the zero-frequency level, such as in region 162, and/or a rapidly varying and/or randomly distributed phase difference over a period of time coinciding with a low or negative COx value (e.g., between −1 and 0), the controller 16 may determine that the COx value has a high confidence level (e.g., greater than 50, 90, 95, or 99 percent), and thus, that the patient's autoregulaton is intact. On the other hand, if the synchrosqueezed cross-wavelet transform does not corroborate the COx as set forth above, the controller 16 may determine that the COx value has a low confidence level (e.g., less than 50, 90, 95, or 99 percent) or is unreliable. Accordingly, the synchrosqueezed cross-wavelet transform may be useful in providing a confidence level for the COx 154 and for evaluating the patient's autoregulation status.

As noted above, a low oscillation Morlet wavelet with a central frequency ($\omega_0$) of 3 radians per second may be utilized to provide sufficient resolution in the cross-wavelet transform and/or synchrosqueezed cross-wavelet transform. In certain embodiments, a low oscillation wavelet with a central frequency of approximately 1, 2, 3, or 4 radians per second may be utilized. In some embodiments, a low oscillation wavelet with a central frequency of less than approximately 5 radians per second may be utilized as high central frequencies may cause the phase information to become smoothed over time and provide insufficient resolution for evaluation of the patient's autoregulation.

FIG. 8 is a process flow diagram of a method 170 of monitoring autoregulation using a synchrosqueezed cross-wavelet transform, in accordance with an embodiment. Some or all of the steps of the method 170 may be implemented by the controller 16 (e.g., the processor 24 of the controller 16) of FIG. 1, for example, to determine whether the patient's autoregulation is impaired. In step 172, the controller 16 may receive the blood pressure signal (e.g., arterial blood pressure signal). In some embodiments, the controller 16 may receive the blood pressure signal from the blood pressure sensor 12, as set forth above. In step 174, the controller 16 may receive the oxygen saturation signal. In some embodiments, the controller 16 may receive the oxygen saturation signal from the oxygen saturation sensor 14, as set forth above.

In step 176, the controller 16 may determine the COx based on the linear correlation between blood pressure measurements of the blood pressure signal and the oxygen saturation measurements of the oxygen saturation signal. In step 178, the controller 16 may calculate a cross-wavelet transform of the blood pressure signal and the oxygen saturation signal. In step 180, the controller 16 may calculate the synchrosqueezed cross-wavelet transform. In step 182, the controller may determine a confidence level associated with the COx based at least in part on the synchrosqueezed cross-wavelet transform. As noted above, regions of high or positive COx values (e.g., between 0 and 1) are expected to correlate with regions of approximately zero and/or constant phase difference (e.g., regions of high energy in the zero-frequency level of the synchrosqueezed cross-wavelet transform). Additionally, regions of near-zero and/or low COx values (e.g., between −1 and 0) are expected to correlate with regions of a phase difference of approximately +/−π radians and/or a rapidly varying and/or randomly distributed phase difference.

Thus, when the synchrosqueezed cross-wavelet transform includes significant energy at the zero-frequency level over a period of time coinciding with a high or positive COx value (e.g., between 0 and 1), the controller 16 may determine that the COx value has a high confidence level (e.g., greater than 50, 90, 95, or 99 percent), and thus, that the patient's autoregulation is impaired. Similarly, when the synchrosqueezed cross-wavelet transform indicates low energy at the zero-frequency level and/or a rapidly varying and/or randomly distributed phase difference over a period of time coinciding with a low or negative COx value (e.g., between −1 and 0), the controller 16 may determine that the COx value has a high confidence level (e.g., greater than 50, 90, 95, or 99 percent), and thus, that the patient's autoregulation is intact. On the other hand, if the synchrosqueezed cross-wavelet transform does not corroborate the COx as set forth above, the controller 16 may determine that the COx value has a low confidence level (e.g., less than 50, 90, 95, or 99 percent) or is unreliable.

In step 184, the controller 16 may provide an indication of autoregulation status. For example, the controller 16 may cause the output device 18 to provide a visual or audible indication of the autoregulation status (e.g., functioning or impaired), the COx, the phase difference, the phase map, the cross-wavelet transform, the synchrosqueezed cross-wavelet transform, and/or a confidence level. In some cases, when the controller 16 determines that the synchrosqueezed cross-wavelet transform corroborates the COx, the controller 16 may cause the output device 18 to provide a visual or audible indication that the signal indicative of the patient's autoregulation status and/or the COx signal 64 has a high confidence level and/or is reliable. In certain embodiments, while the synchrosqueezed cross-wavelet transform does not corroborate the COx, the controller 16 may not output the COx signal 64 and/or the signal indicative of the patient's autoregulation status. Additionally or alternatively, the controller 16 may cause the output device 18 to display a blank display screen or provide an appropriate visual or audible indication that the COx signal 64 is unavailable. Additionally or alternatively, the controller 16 may hold or maintain the COx value immediately preceding the segment determined to be unreliable, and thus may cause the output device 18 to show the most recent reliable COx signal 64 for a set period of time or until the phase difference indicates that the COx is reliable. Additionally or alternatively, the controller 16 may be configured to weight COx value(s) based on the synchrosqueezed cross-wavelet transform and/or to average the unreliable COx value(s) with the most recent reliable COx value(s), and may cause the output device 18 to provide an appropriate visual or audible indication of this average COx value.

Figure 9:
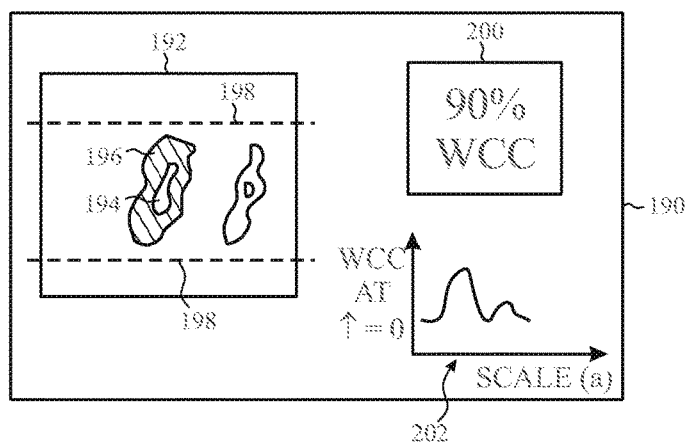
FIG. 9 is an embodiment of a display configured to display various information related to an autoregulation status of a patient.

FIG. 9 is an embodiment of a display 190 configured to display various information related to an autoregulation status of a patient. The display 190 may be part of and/or may include any of the features of the output device 18, discussed above. Furthermore, the display 190 may display any of the information related to the patient's autoregulation status set forth above. Various wavelet-based techniques for evaluating a patient's autoregulation status are disclosed herein. In some embodiments, a wavelet cross-correlation (WCC) measure may additionally or alternatively be used to monitor the relationship between blood pressure and oxygen saturation, and thereby, to evaluate the patient's autoregulation status. For example, the WCC may exhibit a first peak at 0.33 Hz and a second peak at 0.1 Hz. In healthy patients with properly functioning autoregulation systems, the first peak may disappear during a head-up maneuver, while the second peak may shift to higher wavelet scales. However, in patients with impaired autoregulation systems, there may not be a significant peak at 0.33 Hz, and the peak at 0.1 Hz may not shift significantly during the maneuver. Thus, the WCC may be useful in monitoring the patient's autoregulation status. Accordingly, in some embodiments, information indicative of the WCC may be displayed on the display 190. In certain embodiments, a WCC plot may show relative degrees of correlation via distinct contours and/or colors, as shown in region 192 of the display 190. In some embodiments, a plurality of colors (e.g., 2, 3, 4, 5, or more) may show multiple degrees of correlation. In some embodiments, two colors may be utilized to indicate whether the WCC is above or below a predetermined threshold of correlation (e.g., a first color is used in a first portion 194 of the WCC above the predetermined threshold and a second color is used in a second portion 196 of the WCC below the predetermined threshold).

In some embodiments, a time at which a maximum correlation in the WCC at a particular scale (e.g., characteristic frequency or other frequency band suitable for evaluating autoregulation status, such as scales corresponding to waves between 20 to 250 second periods) or scales may be displayed on the screen of the display 190. In certain embodiments, the scales may be selected and/or input by a user (e.g., via inputs coupled to the controller 16 and/or the display 190). In some embodiments, the scales may be predetermined (e.g., stored on the memory device 26) and utilized by the controller 16 during evaluation of the patient's autoregulation status. The display 190 may display the band of interest, or the display 190 may display a wider range of frequencies while highlighting the band of interest, as shown in region 198 of the display.

In certain embodiments, the controller 16 may cause a summed or characteristic value of WCC to be displayed on the display 190, as shown in region 200 of the display 190. A region over which the characteristic value is calculated may be selected by the user (e.g., by specifying the region on a touch sensitive display). In some embodiments, the region over which the characteristic value is calculated is determined automatically (e.g., based on areas associated with high levels of correlation, such as greater than 10, 20, 30, 40, 50, 60, 70, 80, 90 percent, or more, and/or areas encompassing predetermined and/or selected scales of interest).

In some embodiments, the controller 16 may cause the display 190 to update the WCC plot and/or the WCC value in real time, or at predetermined periods (e.g., every 5, 10, 20, or 30 seconds). The displayed information may be based on the latest calculated values representative of those collected during a previous update period (e.g., a median or a mean of the values collected during the time since the last update). In some embodiments, only zero-time delay values may be used to determine autoregulation status, and a graph of such WCC values against scale (or characteristic frequency) may be displayed, as shown in region 202 of the display 190. It should be understood that the display 190 may be configured to display all or some of the information illustrated in FIG. 8, and in any suitable arrangement. Although examples provided herein relate to providing information indicative of the WCC on the display 190, it should be understood that, additionally or alternatively, an audible indication of such information may be provided via one or more speakers, for example.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that certain elements of the disclosed embodiments may be combined or exchanged with one another.

What is claimed is:

1. A method for monitoring autoregulation, the method comprising:
receiving, by a processor, a blood pressure signal of a patient;
receiving, by the processor, an oxygen saturation signal of the patient;
determining, by the processor, a phase difference between the blood pressure signal and the oxygen saturation signal;
determining, by the processor, a cerebral oximetry index (COx) value based on the blood pressure signal and the oxygen saturation signal;
determining, by the processor, a confidence level for the COx value based on the phase difference between the blood pressure signal and the oxygen saturation signal; and
determining, by the processor, an autoregulation status of the patient based at least in part on the confidence level determined based on the phase difference between the blood pressure signal and the oxygen saturation signal.

2. The method of claim 1, wherein determining the phase difference comprises processing the blood pressure signal and the oxygen saturation signal using a complex transform to determine the phase difference.

3. The method of claim 2, wherein the complex transform is a wavelet transform.

4. The method of claim 3, wherein the wavelet transform comprises a low oscillation Morlet wavelet with a central frequency of less than five radians per second.

5. The method of claim 1, wherein determining the phase difference comprises:
calculating a cross-wavelet transform of the blood pressure signal and the oxygen saturation signal, and
synchrosqueezing the cross-wavelet transform to generate a synchrosqueezed cross-wavelet transform indicative of the phase difference.

6. The method of claim 1, further comprising outputting, by the processor for display, a measure indicative of the autoregulation status of the patient.

7. The method of claim 1, further comprising providing an indication of impaired autoregulation status to an output device while the COx value is greater than zero and the phase difference is approximately equal to zero.

8. The method of claim 1, further comprising providing the COx value on a display while the COx value is zero or less than zero, and the phase difference is approximately $+/-\pi$ radians, rapidly varying, or randomly distributed.

9. A non-transitory computer-readable medium having computer executable code stored thereon, the code comprising instructions to:
receive a blood pressure signal of a patient;
receive an oxygen saturation signal of the patient;
determine a phase difference between the blood pressure signal and the oxygen saturation signal;
determine a cerebral oximetry index (COx) value based on the blood pressure signal and the oxygen saturation signal;
determine a confidence level for the COx value based on the phase difference between the blood pressure signal and the oxygen saturation signal; and
determine an autoregulation status of the patient based at least in part on the confidence level determined based on the phase difference between the blood pressure signal and the oxygen saturation signal.

10. The non-transitory computer-readable medium of claim 9, wherein the instructions to determine the phase difference comprise instructions for applying a cross-wavelet transform to the blood pressure signal and the oxygen saturation signal to determine the phase difference.

11. The non-transitory computer-readable medium of claim 9, wherein the code further comprises instructions for providing an indication of impaired autoregulation status to an output device while the COx value is greater than zero and the phase difference is approximately equal to zero.

12. The non-transitory computer-readable medium of claim 9, wherein the instructions to determine the phase difference comprise:
instructions for calculating a cross-wavelet transform of the blood pressure signal and the oxygen saturation signal, and
instructions for synchrosqueezing the cross-wavelet transform to generate a synchrosqueezed cross-wavelet transform indicative of the phase difference.

13. A system for monitoring autoregulation, the system comprising:
an oxygen saturation sensor configured to obtain an oxygen saturation signal from a patient;
a controller comprising a processor configured to:
receive a blood pressure signal of the patient;
receive the oxygen saturation signal of the patient;
determine a phase difference between the blood pressure signal and the oxygen saturation signal;
determine a cerebral oximetry index (COx) value based on the blood pressure signal and the oxygen saturation signal;
determine a confidence level for the COx value based on the phase difference between the blood pressure signal and the oxygen saturation signal; and
determine autoregulation status of the patient based at least in part on the confidence level determined based on the phase difference between the blood pressure signal and the oxygen saturation signal.

14. The system of claim 13, further comprising a display, wherein the processor is configured to output an indication of the autoregulation status of the patient on the display.

15. The system of claim 13, wherein the processor is configured to:
calculate a cross-wavelet transform of the blood pressure signal and the oxygen saturation signal,
synchrosqueeze the cross-wavelet transform to generate a synchrosqueezed cross-wavelet transform, and
utilize the synchrosqueezed cross-wavelet transform to determine a confidence level related to the COx value.

16. The system of claim 13, wherein the controller is further configured to refrain from outputting, via a display, an indication of the autoregulation status of the patient when the phase difference does not corroborate the COx value.

17. The system of claim 13, wherein the controller is further configured to provide a visual or audible indication that the COx value is unavailable when the phase difference does not corroborate the COx value.

18. The system of claim 13, wherein the controller is further configured to hold or maintain the COx value immediately preceding a segment of the blood pressure signal or an oxygen saturation signal determined to be unreliable when the phase difference does not corroborate the COx value.

19. The system of claim 13, wherein the controller is further configured to present, via a display and when the phase difference does not corroborate the COx value, a most recent reliable COx value for a set period of time or until the phase difference indicates that a new COx value is reliable.

20. The system of claim 13, wherein the controller is further configured to: determine an average COx value based on an unreliable COx value and a most recent reliable COx value; and present, via a display, an indication of the average COx value when the phase difference does not corroborate the COx value.

* * * * *